United States Patent [19]

Giachino et al.

[11] Patent Number: 5,458,646
[45] Date of Patent: Oct. 17, 1995

[54] WRIST PROSTHESIS

[75] Inventors: A. Alan Giachino, 33 Davidson Drive, Gloucester, Ontario, Canada, K1J 6L7; Alan J. Yeadon, Ottawa, Canada

[73] Assignee: A. Alan Giachino, Ontario, Canada

[21] Appl. No.: 146,534

[22] Filed: Nov. 1, 1993

Related U.S. Application Data

[63] Continuation-in-part of Ser. No. 764,921, Sep. 24, 1991, abandoned.

[51] Int. Cl.$^6$ ................................................. A61F 2/42
[52] U.S. Cl. ................................................. 623/21
[58] Field of Search ......................... 623/18, 19, 20, 623/21

[56] References Cited

U.S. PATENT DOCUMENTS

| | | | |
|---|---|---|---|
| 4,040,130 | 9/1977 | Laure | 3/1.91 |
| 4,063,314 | 12/1977 | Loda | 3/1.91 |
| 4,100,626 | 7/1978 | White | 3/1.91 |
| 4,156,296 | 5/1979 | Johnson et al. | 623/21 |
| 4,164,793 | 8/1979 | Swanson | 3/1.91 |
| 4,178,640 | 12/1979 | Buechler et al. | 3/1.91 |
| 4,180,871 | 1/1980 | Hamas | 3/1.91 |
| 4,229,840 | 10/1980 | Gristina | 3/1.91 |
| 4,229,841 | 10/1980 | Youm et al. | 3/1.91 |
| 4,259,752 | 4/1981 | Taleisnik | 3/1.91 |
| 4,307,473 | 12/1981 | Weber | 3/1.91 |
| 4,645,505 | 2/1987 | Swanson | 623/21 |
| 4,714,476 | 12/1987 | Ranawat et al. | 623/21 |
| 4,784,661 | 11/1988 | Beckenbaugh et al. | 623/21 |
| 4,938,769 | 7/1990 | Shaw | 623/20 |
| 5,133,762 | 7/1992 | Branemark | 623/21 |
| 5,176,710 | 1/1993 | Hahn et al. | 623/20 |
| 5,314,485 | 5/1994 | Judet | 623/21 |

FOREIGN PATENT DOCUMENTS

| | | | |
|---|---|---|---|
| 1053852 | 5/1979 | Canada . | |
| 0034192 | 8/1981 | European Pat. Off. . | |
| 2630640 | 11/1989 | France | 623/20 |
| 2680968 | 3/1993 | France | 623/21 |
| 2215610 | 9/1989 | United Kingdom | 623/20 |
| 93024079 | 12/1993 | WIPO | 623/18 |

OTHER PUBLICATIONS

Cooney II et al, "Total Wrist Arthroplasty: Problems with Implant Failures", *Clin. Orthop.* No. 187, Jul./Aug. 1984; pp. 121–128.

Beckenbaugh, "Total Wrist Arthroplasty: Review of Current Concepts", *The Wrist and its Disorders*, 1988; Chap. 29, pp. 439–445.

Swanson et al, "Flexible Implant Arthroplasty of the Radiocarpal Joint, Surgical Technique and Long–Term Study", *Clin. Orthop.* No. 187, Jul./Aug. 1984; pp. 94–105.

J. Y. Alnot et le Group GUEPAR, "L'Arthroplastie Totale Guepar de Poignet Dans la Polyarthrite Rhumatoide", *Acta Orthopædica Belgica*, vol. 54–2, 1988.

Taleisnik, "*The Wrist*", Churchill Livingstone, 1985, pp. 14–23 & 429–432.

*Primary Examiner*—David Isabella
*Assistant Examiner*—Laura Fossum
*Attorney, Agent, or Firm*—Christie, Parker & Hale

[57] ABSTRACT

A wrist prosthesis having a distal supporting part and a part for proximal support of the prosthesis on both the radius and the ulna. The proximal part of the prosthesis may be a plate configured to be supported on substantially unaltered surfaces of the radial and ulnar epiphyses when the radius and ulna are fused at the radial-ulnar joint. The distal part of the prosthesis may be shaped to be supported by surfaces on at least three of the distal carpal bones. The prosthesis may include an intermediate component having a receptacle portion distally defining a concave bearing surface. The distal part may have a proximal side defining an ellipsoidal convex bearing surface having a generally part-circular cross-section. This invention also provides a method of implanting a wrist prosthesis which is configured to be attached to the distal ends of the radius and ulna which includes the steps of fixably attaching the prosthesis to the ends of the radius and ulna and removing a segment of the ulnar diaphysis to permit supination and pronation.

17 Claims, 6 Drawing Sheets

WRIST PROSTHESIS

RELATED APPLICATIONS

This application is a continuation-in-part of application Ser. No. 764,921, filed Sep. 24, 1991.

FIELD OF THE INVENTION

This invention relates to endoprosthetic joints, and more particularly for a wrist joint for surgical replacement of bones and joints damaged by disease.

BACKGROUND OF THE INVENTION

The wrist includes seven carpal bones in two rows. The proximal carpal row consists of the triquetrum, lunate and scaphoid bones. The distal carpal row consists of the hamate, capitate, trapezoid and trapezium bones. An eighth carpal bone, the pisiform, rests anterior to the triquetrum. Collectively, the carpal bones are known as the carpus. The bones of the hand include five metacarpal bones that articulate at their proximal ends with the distal row of carpal bones. The forearm has two bones, the radius and ulna. The distal end of the radius articulates with the scaphoid and lunate bones and the distal head of the ulna. The joints between the carpal bones themselves and between the carpus and the radius permit wrist and hand movement. The carpus is supported by ligaments some of which run from various carpal bones to the distal ends of the radius and the ulna. In normal wrists, the approximate center of rotation for radial-ulnar deviation and flexion-extension motion is located at a point in the capitate bone known as the head of the capitate. This center of rotation is offset towards the palm and the ulnar side of the long axis of the radius.

Total wrist endoprosthetic arthroplasty involves the prosthetic replacement of the wrist by an artificial joint designed to simulate normal wrist motion while maintaining stability of the components and proper hand on forearm alignment. To achieve a stable full range of motion, one must reproduce as best as possible the anatomical situation. Where possible, ligaments should not be sacrificed. The prosthesis should place the ligaments in their proper degree of tension. The articulating surfaces should approximate the center of rotation and distribute forces over a wide area. This would provide some inherent stability while allowing the ligaments to limit the range of motion. In addition, the prosthesis should avoid invading non-diseased joints.

Prior devices are available for either total or partial replacement of the wrist joint. These devices employ various means of articulation including ball and socket joints. Orthopedically suitable materials are available including biologically inactive metals and plastics. One such plastic is high density polyethylene which is particularly suitable for concave shaped bearing surfaces in the articulation means of a prosthesis. Various means of attachment of a prosthesis to bone are available including pins, screws, intramedullary stems, and bone cement.

Two early prosthetic devices having variations of a ball and socket articulating means (Meuli; and Volz) are described by Cooney, W. P. et al "Total Wrist Arthroplasty; Problems with Implant Failures"; Clin. Orth. Rel. Research 187; 121–128 (1984) wherein it was reported that with such implants, there is an unacceptably high failure rate and a survival rate which decreases over time.

A variety of prosthetic devices are described in the following group of references:

Swanson, A. B. et al; "Flexible Implant Arthroplasty of the Radiocarpal Joint:, Clinical Orthopaedics and Related Research (1984), No. 187, p. 94–105.

U.S. Pat. No. 4,040,130 (Laure)
U.S. Pat. No. 4,063,314 (Loda)
U.S. Pat. No. 4,100,626 (White)
U.S. Pat. No. 4,178,640 (Buechler, et al)
U.S. Pat. No. 4,180,871 (Hamas)
U.S. Pat. No. 4,229,841 (Youm, et al)
U.S. Pat. No. 4,229,840 (Gristina)
U.S. Pat. No. 4,307,473 (Weber)
U.S. Pat. No. 4,259,752 (Taleisnik)
U.S. Pat. No. 4,645,505 (Swanson)
U.S. Pat. No. 4,714,476 (Ranawat, et al)
U.S. Pat. No. 4,784,661 (Beckenbaugh, et al)
U.S. Pat. No. 5,133,762 (Branemark)
European Patent Application No. 0 034 192 (Bedeschi and Luppino)
Canadian Patent No. 1,053,852 (Frey)

With the exception of Branemark, all the aforementioned prior art devices employ proximal fixation into only the radius. In the case of the devices of Laure and White, and that described in the reference by Swanson, et al, the center of rotation is in a nonanatomical position in line with the axis of the radius. The devices described in the other references and the aforementioned Meuli device provide articulating means offset from the axis of the radius placing the center of rotation in a more anatomical position. However, in the devices that have proximal fixation to only the radius, proximal support of the prosthesis is not centered underneath the center of rotation of the wrist.

The devices described in the aforementioned references (with the exception of the Swanson patent) all employ metacarpal fixation of the distal portion of the prosthesis. In the Beckenbaugh, et al patent, it is stated that the capitate-third metacarpal fixed unit is the logical positioning choice for the metacarpal component of the wrist prosthesis. In the Swanson patent, there is no distal fixation means because the distal portion of the device is a cup-shaped recess dimensioned to receive and articulate with a portion of the proximal row of the carpal bones. Thus in all cases where the prosthesis is fixed at its distal end, there is an invasion of one or more joints between the distal carpal bones and the metacarpal which, in many cases, are not diseased.

There is no mechanical joint which functions as an articulating means in the device of the Swanson patent. The device described in the reference by Swanson, et al is a single piece flexible silicone implant. Ball and socket joints are employed as articulating means in the devices described by Hamas, White, Frey, Laure, Loda, and Gristina. The aforementioned Volz device and the device described in the Weber patent have variations of ball and socket joints with sockets having part-cylindrical bearing surfaces. Youm, et al describes a joint arranged about pivot pins set on perpendicular axes. Buechler, et al describes a toroidal base that rotates in a part concave surface between two shafts. Ranawat, et al describes an articulating means employing a metal axle.

The device described by Taleisnik has proximal and distal components having elongated stems for intramedullary implantation through the capitate into the third metacarpal and into the radius. The proximal and distal components are connected by a variation of a ball and socket joint offset toward the ulna and the palm. The joint comprises a part-cylindrical recess engaged with a component having a circular cross-section and an oval shape in a longitudinal direction. At least the lunate bone is resected in order to permit implantation of the device. Proximal support is not centered underneath the center of rotation and the distal component invades the joint between the capitate and metacarpal.

Bedeschi and Luppino's European patent application describes a prosthesis having a plate-like first element which is fixed to the end of the radius and having a doubly concave bearing surface. The prosthesis includes a second element having a banana-like shape complementary to the bearing surface of the first element and a geometry that permits it to replace the scaphoid and lunate bones. The second element has fixing pins which are driven through distal carpal bones into metacarpal bones. The device does not provide an offset center of rotation.

The device described in the Beckenbaugh, et al patent is compared to the aforementioned designs of Meuli and Volz in Beckenbaugh, R. D.; *Total Wrist Arthroplasty; Review of Current Concepts*; in "The Wrist and its Disorders" (1988), ed. by D. M. P. Lichtman; W.B. Saunders Company; Chapter 29, p. 439–445. The device of Beckenbaugh, et al comprises first and second components each having fixation stems for attachment to the third metacarpal and the radius. The articulating means is a joint consisting of an ellipsoidal, convex bearing surface and a complementary, concave bearing surface on the other component. The ellipsoidal surfaces have generally part-circular cross-sections. The prosthesis invades a carpal-metacarpal joint and is only attached to the radius. The center of rotation of the articulating surfaces is offset towards the palm and the ulna from the axes of the radial and metacarpal fixation stems. This device provides a large bearing surface in an appropriate anatomical position but the distal end of the radius must be resected in order to implant the device resulting in loss of ligamenture supporting the wrist. Furthermore, the ends of the elliptically profiled convex bearing surface limits the range of radial-ulnar deviation which is normally the function of the ligamenture.

The device described in the Branemark patent is proximally attached to the radius and the ulna and distally attached to the third metacarpal. The primary articulating means is an elastomeric material between the means for proximal and distal attachment. The distal ends of both the radius and ulna are resected and prepared to provide flat surfaces, with the prepared ulna being substantially shorter than the radius. The means for proximal attachment includes a plate having a stepped outer or proximal surface that is intended to engage with the prepared surfaces of the radius and ulna. Thus, a first, thin portion of the plate has a flat proximal surface that is supported on the prepared surface of the radius, and a second, thick portion of the plate has a flat surface offset from the first portion, to be supported on the prepared surface of the ulna. The thick portion of the plate houses a secondary articulating means which is a swivelling joint having an axial member that is part of the ulnar attachment means. The radius is permitted to rotate relative to the ulna for supination and pronation by the presence of the swivel joint, but this necessitates the positioning of the ulna at a distance from the radius to prevent the two bones from striking. Since the ulna must be considerably shortened to accommodate the swivel joint mechanism, all of the ligaments attached to the distal end of the ulna must be sacrificed. Furthermore, the Branemark device would be subject to stress that would eventually loosen the ulnar and radial attachment of the joint since supination and pronation causes the relative length of the radius to the ulna to change exerting leverage against the fastening devices.

SUMMARY OF THE INVENTION

It is an object of the present invention to provide embodiments of a wrist prosthesis which will overcome disadvantages in the prior devices by providing:

means for proximal fixation of the prosthesis that obviates the need for an offset in order to provide a center of rotation of the wrist near the anatomical center of rotation (the region of the head of the capitate) and provides proximal support for the prosthesis centered beneath the center of rotation for better support of the wrist;

proximal fixation means for the prosthesis that allow one to avoid loss of the ligamenture between the carpus and the radius and ulna;

distal fixation of the prosthesis which will provide better support for the wrist without fixation to a metacarpal bone thereby avoiding invasion of a carpal-metacarpal joint; and articulation means for a prosthesis comprising complementary bearing surfaces of sufficient size and appropriate shape to provide adequate support for the wrist while facilitating radial-ulnar deviation.

This invention provides a prosthesis for implantation in a wrist, the prosthesis having proximal and distal parts with articulating means therebetween, said distal part being configured to be fastened to one or more bones of the carpus or hand wherein said proximal part includes means to fix the proximal part to both the radius and ulna.

This invention also provides a plate suitable for use in the proximal part of the aforementioned prosthesis, the plate being configured to be supported on substantially unaltered bony surfaces of each of the radial and ulnar epiphyses when the radius and ulna are fused at the radial-ulnar joint. The plate's shape and its dimensions are preferably such that the plate will not interfere with at least the ligamenture extending from the distal ends of the radius and ulna to the distal carpal row and metacarpals.

This invention also provides a prosthesis for implantation in a wrist and to replace the proximal row of carpal bones, the prosthesis having proximal and distal parts with articulating means therebetween, said proximal part being configured to be fastened to one or both bones of the forearm wherein, said distal part is configured to be supported on surfaces of at least three of the distal carpal bones.

This invention also provides a distal part suitable for use in the prosthesis described in the preceding paragraph wherein the proximal surface of the distal part has an ellipsoidal convex shape with a generally part-circular cross-section.

This invention also provides a prosthesis for implantation in a wrist, the prosthesis having proximal and distal parts with articulating means therebetween, said proximal part being configured to be fastened to one or more bones of the forearm; said distal part being configured to be fastened to one or more bones of the carpus or hand; wherein, said articulating means includes two bearing surfaces, the first of said surfaces being connected to said distal part and having an ellipsoidal convex shape with a generally part-circular cross-section, the ends of said ellipsoidal shape having a rounded profile deviating from an ellipse; the second of said surfaces being connected to said proximal part and having a concave shape that is complementary to the ellipsoidal portion of the said first bearing surface.

This invention also provides a prosthesis for implantation in a wrist which includes:

(a) a proximal part which includes a plate configured to be supported on the distal surfaces of each of the radius and ulna when said radius and ulna are fused at their distal ends;

(b) a distal part configured to be supported by surfaces on the distal carpal bones and having a proximal side defining an ellipsoidal convex bearing surface having a generally part-circular cross-section; and, (c) an intermediate component configured to be attached to said proximal part, and having a receptacle portion distally defining a concave bearing surface that is complementary to the convex bearing surface of said distal part; wherein the said distal part and intermediate component replace the proximal row of carpal bones and the said convex bearing surface is received in the concave bearing surface when the prosthesis is implanted in a wrist.

This invention also provides a method of implanting a wrist prosthesis having a proximal part configured to be attached to the distal ends of the radius and ulna which includes the steps of fixing said proximal part to the distal ends of the radius and ulna thereby fusing the radius and ulna at the radial-ulnar joint, and removing a segment of the ulna at a point proximal to the radial-ulnar joint to permit supination and pronation.

BRIEF DESCRIPTION OF THE DRAWINGS

FIGS. 6a–c illustrate a plate suitable for use in the proximal part of a prosthesis of this invention.

FIGS. 7a–d illustrate an intermediate component with a concave bearing surface suitable for use in a prosthesis of this invention.

FIGS. 8a–c illustrate a distal part suitable for use in a prosthesis of this invention.

DESCRIPTION OF THE INVENTION

Figure 1:
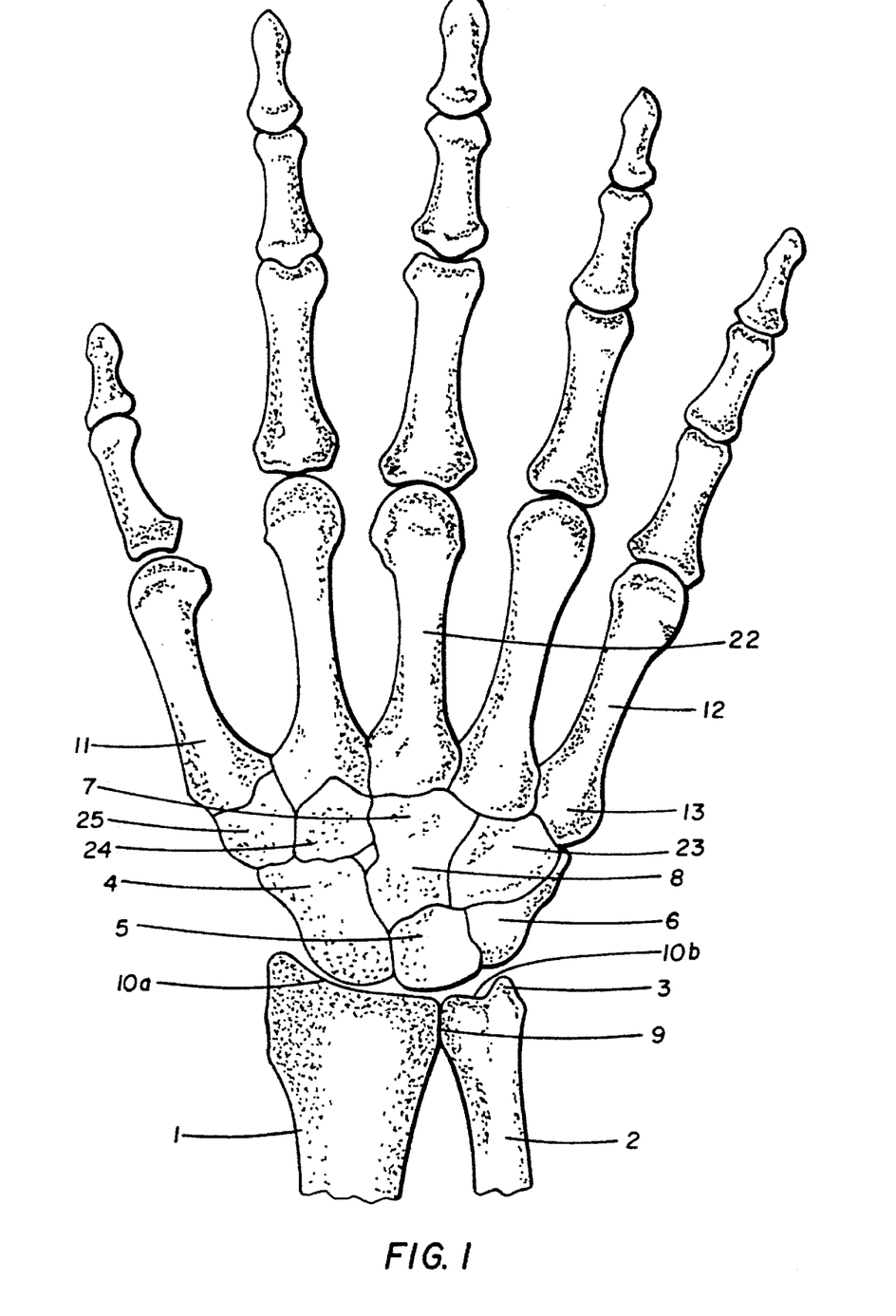
FIG. 1 is a schematic dorsal view of the skeleton of a healthy right wrist, hand and distal portion of the forearm.

FIG. 1 is a schematic dorsal view of the skeleton of a healthy right wrist, hand and distal portion of the forearm. The radius (1) and the ulna (2) articulate distally at the distal radial-ulnar joint (9) and it is through this joint that rotation of the hand, wrist and radius occurs relative to the ulna (pronation and supination). The radial-ulnar joint is the best location to fuse the distal ends of the radius and ulna and retain normal configuration of the wrist when at rest. The distal surface of the distal end of the radius (10a) is the main bearing surface for the wrist bones and near the periphery of this bearing surface attach fibrous ligaments which run from the radius to the carpus to provide stability. The distal surface of the radius comprises cartilage and subchondral bone of the radial epiphysis. Similarly, the ulnar epiphysis is present at the distal surface of the ulna (10b). Further stability to the wrist is provided by ligaments arising from the distal ulna, including the styloid process (3), which cross distally to various points of attachment in the wrist. FIG. 1 also illustrates the bones of the carpus including the proximal carpal row: scaphoid (4), lunate (5), triquetrum (6). The pisiform is not shown in this drawing. The distal row of carpal bones are situated between the proximal carpal row and the metacarpal bones. The first metacarpal (11) is located on the radial (thumb side) of the hand and the fifth metacarpal (12) on the ulnar side. The capitate (7) articulates firmly with the third metacarpal (22) and with the two adjacent carpal bones of the distal carpal row, the hamate (23) and the trapezoid (24). The remaining bone of the distal carpal row is the trapezium (25).

There exists little independent movement in the wrist in both flexion-extension and radial-ulnar deviation. These two axes of wrist motion are known to pass through a region called the head of the capitate (8) which is generally the center of rotation of the wrist for the two aforementioned types of motion. These motions are distinct from the rotation of the hand, wrist and radius (1) that occurs relative to the ulna (2) as described in the preceding paragraph.

Figure 2:
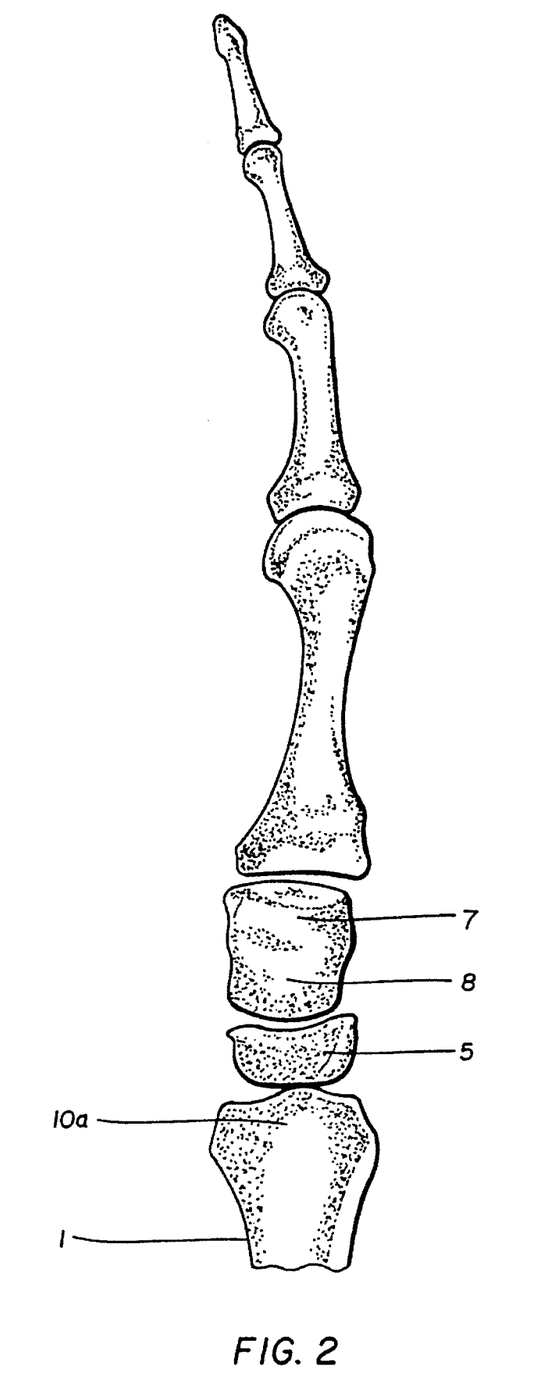
FIG. 2 is a schematic, lateral view of the skeleton of a healthy wrist with a number of bones omitted.

FIG. 2 is a lateral view of the hand illustrating how the lunate (5) rests on the distal articulation of the radius at surface (10a) and that the capitate (7) articulates with the distal surface of the lunate (5). The region of the head of the capitate (8) is shown.

Figure 3:
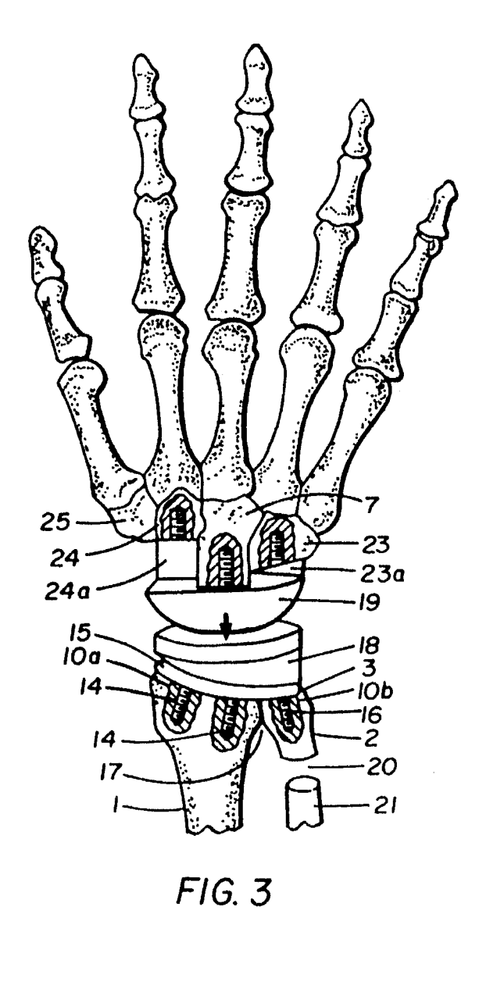
FIG. 3 is a schematic dorsal view of the skeleton of a right wrist, hand and distal portion of the forearm with an implanted prosthesis according to the present invention and is partially cut away to show the fastening means.
Figure 4:
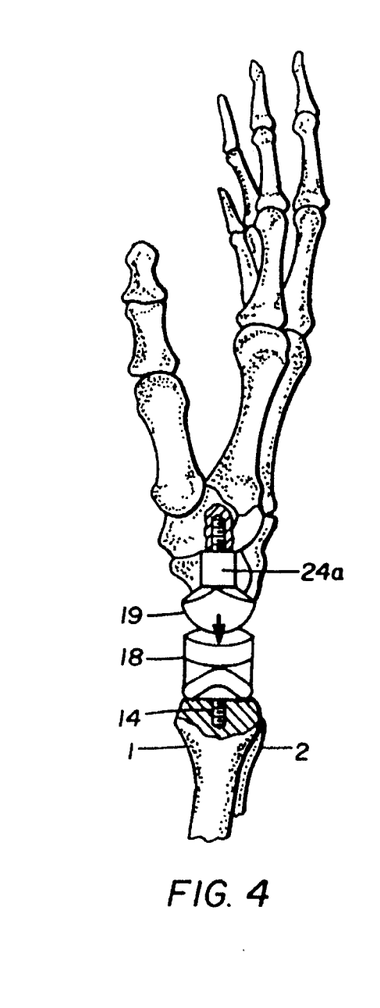
FIG. 4 is a schematic, radial-lateral view of the skeleton of the wrist with an implanted prosthesis according to the present invention and is partially cut away to show the fastening means.
Figure 5:
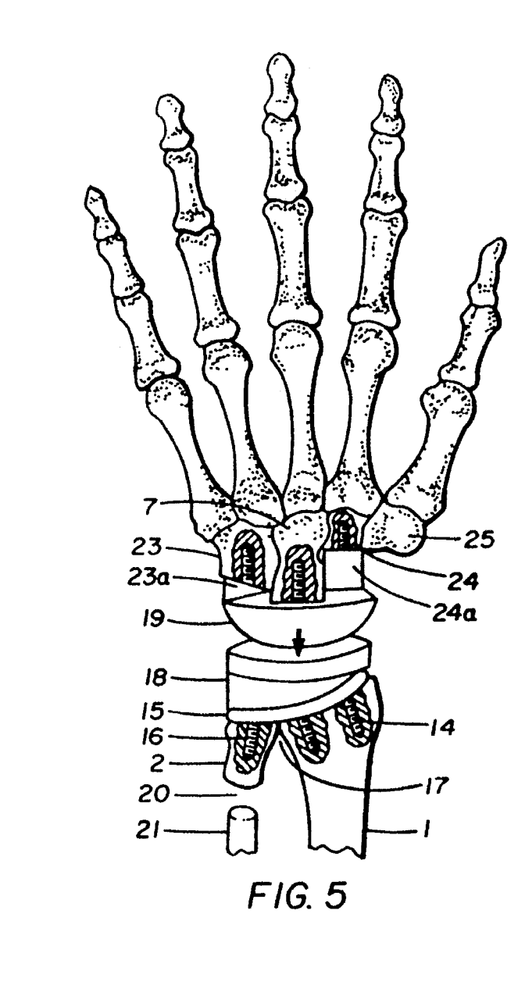
FIG. 5 is a schematic, palmar view of the skeleton of a right wrist, hand and distal portion of the forearm with an implanted prosthesis according to the present invention and is partially cut away to show the fastening means.

Referring now more particularly to FIGS. 3, 4, and 5, there is illustrated a preferred embodiment of the wrist prosthesis of this invention implanted in a wrist. The prosthesis includes a proximal part which in this embodiment includes a plate (15) configured to be supported on the substantially unaltered epiphyses of each of the radius and ulna when the radius and ulna are fused at the radial-ulnar joint in the region (17). The ulnar epiphysis and the portion of the radial epiphysis adjacent the ulna remain in generally the same plane as would be the case when the wrist is at rest. Means are provided for fastening the plate to the distal ends of the radius and ulna which, in this embodiment, include orthopedically suitable screw fasteners (14) and (16) inserted into the distal ends of the radius (1) and the ulna (2) respectively. Supination and pronation of the radius about the ulna is made possible by cutting through the ulnar diaphysis near its distal end and proximal to region (17), and removing a segment of bone to produce gap (20) as shown in FIGS. 3 and 5.

The prosthesis further includes an intermediate component (18) which may be attached to plate (15) after the plate is fixed to the radius and ulna. Intermediate component (18) has a receptacle portion at its distal end which defines a concave bearing surface in the region of the head of the arrow shown on FIGS. 3, 4, and 5. This intermediate component partially replaces the proximal row of carpal bones. Alternatively, the proximal supporting structure provided by plate (15) combined with intermediate component (18) may be provided by a one-piece component, or a multipiece component having the proximal and distal features presented by the combination of the plate and intermediate elements described herein.

The prosthesis further includes a distal part (19) that is shaped so that it will partially replace the proximal row of carpal bones and is supported by surfaces on the distal row of carpal bones. Distal part (19) has a proximal side defining an ellipsoidal convex bearing surface having a generally part-circular cross-section which is complementary to the concave bearing surface of the intermediate component (18) and is received within said concave bearing surface in the direction of the arrow on FIGS. 3, 4, and 5. Means are provided for fastening the distal part to one or more of the distal carpal bones which, in FIGS. 3, 4, and 5, include orthopedically suitable screw fasteners.

As shown in reversed fashions in FIGS. 3 and 5 and in radial-lateral view in FIG. 4, distal part (19) partially replaces the proximal row of carpal bones. A portion of the proximal part of the distal carpal bones may also be replaced since surfaces on the distal row of carpal bones are surgically prepared by shaping the bones to support surfaces on the distal side of the distal component (19). The proximal side of the trapezoid (24) is shaped to abut the flat distal face of trapezoid engaging projection (24a) which is seen in FIGS. 3, 4, and 5 as having a generally rectangular profile. The proximal surface of the hamate (23) is shaped to support a hamate engaging projection (23a) which in FIGS. 3 and 5 is illustrated as having a distal surface that projects proximally and medially. The region between projections (23a) and (24a) is a generally rectangular, flat bottom depression which will engage with a prepared proximal surface of the capitate (7).

Figure 6A:
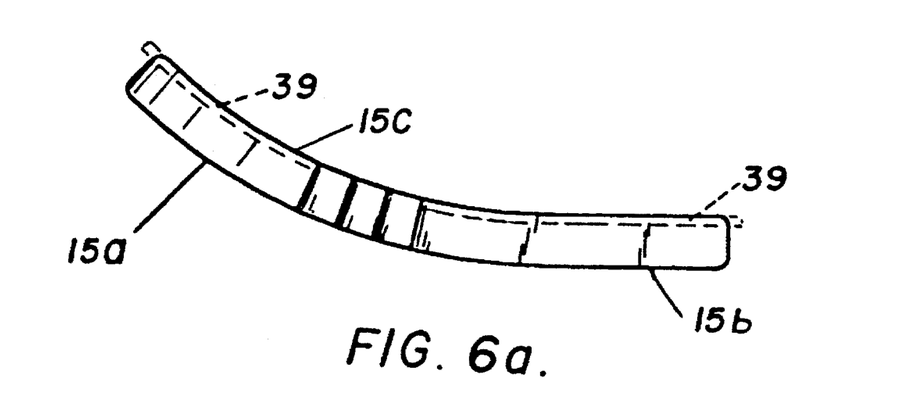
FIG. 6a is a side view of the plate.
Figure 6B:
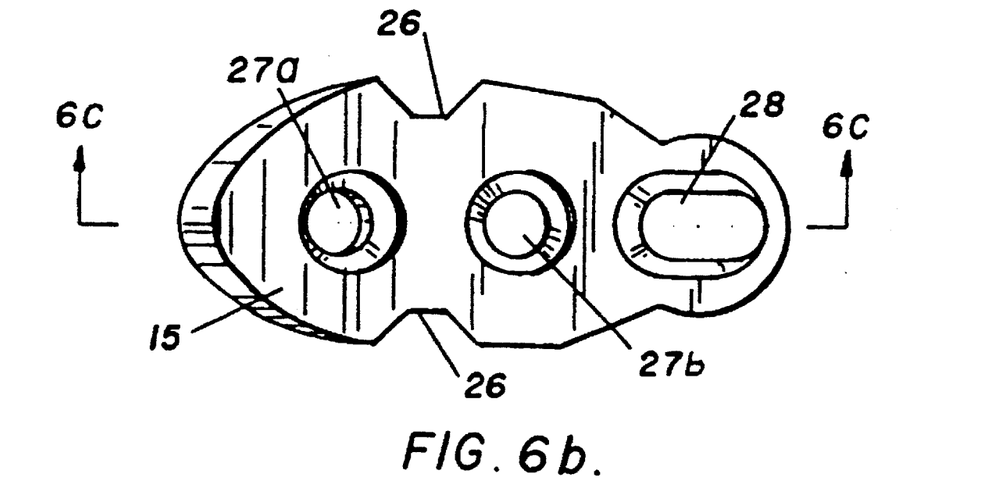
FIG. 6b is a top view of the plate; and, FIG. 6c is a sectional side view along line 6c of FIG. 6b.
Figure 6C:
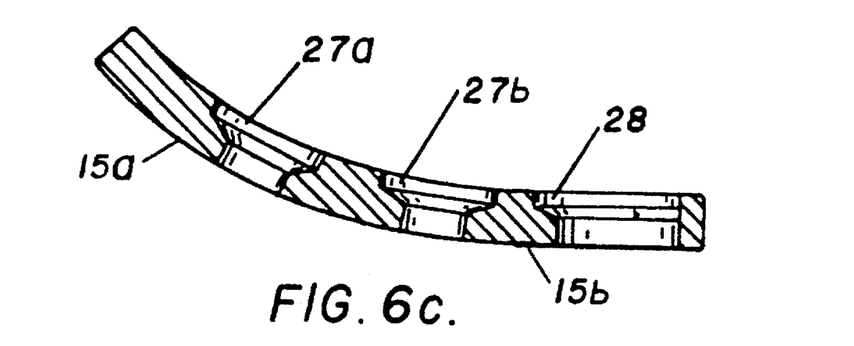
Figure 7A:
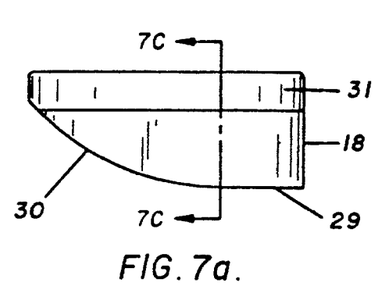
FIG. 7a is a side view showing the longitudinal extent of the intermediate component.
Figure 7B:
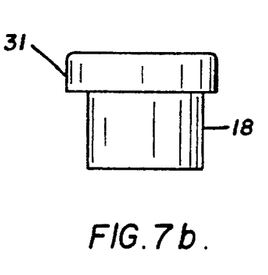
FIG. 7b is a front view.
Figure 7C:
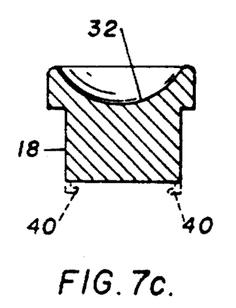
FIG. 7c is a sectional front view along line 7c of FIG. 7a; and, FIG. 7d is a top view.
Figure 7D:
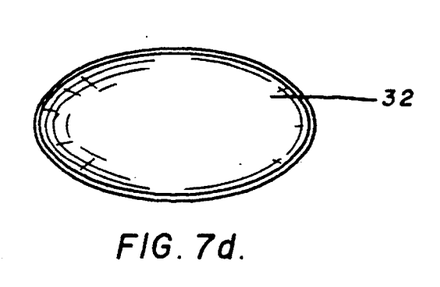

FIGS. 6a, 6b, and 6c illustrate a preferred embodiment of the plate (15) shown in FIGS. 3 and 5. In this embodiment, the plate is of generally constant thickness with opposite and generally complementary inner (distal) and outer (proximal) sides, although a constant thickness is not required. Also, the inner side may be altered to facilitate attachment of prosthesis components to the plate and need not be complementary in shape to the outer side. As shown in FIGS. 6a and 6c, plate (15) has a first, generally planar proximal surface (15b) on its outer side which is to be supported on the ulnar epiphysis and a portion of the radial epiphysis adjacent the ulna so as to straddle the region of the radial-ulnar fusion (17) shown in FIGS. 3 and 5. The plate (15) also has a second, curved proximal surface (15a) on its outer side that conforms to the anatomic curvature of the radial epiphysis. FIG. 6b is a plan view that further illustrates the preferred shape of plate (15). As shown in FIGS. 3 and 5, the length of plate (15) is preferably such that it will cover most of the lateral extent of the distal epiphysial surfaces of the radius and ulna but will not interfere with the styloid process (3) and ligaments. attached thereto. The face of plate (15), as shown in FIG. 6b, has a generally ovoid profile with a general tapering from about the mid-point of the plate towards one end of the plate to provide a narrowed ulnar engaging portion surrounding through-hole (28). The plate preferably has dimensions that will permit the plate to be positioned inside most of the ligamenture of the distal radius and ulna. When use of distal part (19) as described above is contemplated, the plate (15) should be dimensioned to not interfere with at least the sheet of ligaments that extends from the distal ends of the radius and ulna to the distal carpal row and metacarpals. The perimeter of the plate (15) may have notches (26) to prevent interference with bony prominences and soft tissue on the distal end of the radius.

The shape of plate (15) is intended to conform to the anatomical shape of the distal aspects of the radius and ulna which may be determined by reference to anatomical data such as X-ray measurements of a patient. Most patients will be accommodated if three different sizes of plate (15) are made available to the surgeon who may then make minor surgical adjustments to the shape of the patient's radius and ulna to fit one of the plate sizes.

The plate (15) is most preferably composed of an orthopedically suitable metal in order to provide sufficient strength as the plate constitutes the proximal support for the prosthesis. Suitable metals include cobalt chromium alloy and titanium.

Since a preferred method of attachment of plate (15) to the radius and ulna is by means of orthopedically suitable screw fasteners, the plate may have through-holes configured to receive such fasteners. As shown in FIGS. 6b and 6c, through-holes (27a) and (27b) are provided, each having a bevelled perimeter and a countersink so that the heads of suitable screw fasteners will sit flush within the through-holes, when driven into the radius. Through-hole (28) is provided to accept a similar screw fastener for fixation of the plate to the ulna. In this embodiment, planar surface (15b) generally extends from an end of the plate medially to through-hole (27b), crossing through-hole (28). As shown in FIGS. 6b and 6c, through-hole (28) is elongated and lacks a bevelled perimeter at one end. In such an embodiment, a bevel-headed screw fastener driven into through-hole 28 will bias the plate (15) in the direction of its longitudinal axis thereby facilitating fusion of the distal end of the ulna with the distal end of the radius.

It will be appreciated by a person skilled in the art that a variety of fastening means may be employed for fixation of plate (15) to the radius and ulna. For example, fixed pegs may be attached to the plate in the regions where through-holes 27a, 27b and 28 are shown in the Figures. Such pegs are to be driven into holes drilled in the bones. Furthermore, a single through-hole and fastener, or other form of fastener such as a peg, may be provided for attachment of the plate to the radius. In the latter case of a single through-hole for radius attachment, the hole may be shaped in the same way as through-hole (28) shown in FIG. 6.

Persons skilled in the art will appreciate from the preceding description that attachment of a proximal part of a wrist prosthesis to both the radius and ulna provides a larger and more stable base of support than in other devices. This invention allows the proximal support of a prosthesis to be centered beneath the center of rotation of the wrist while providing increased stability and support, since the radius and ulna are fused at the radial-ulnar joint and the proximal support of the prosthesis extends across most of the distal epiphysial surfaces of the radius and ulna. Thus, the underlying bone is more stable than in prior art procedures and the prosthesis has a larger supporting surface. Furthermore, the tendency of a prosthesis attached to both the radius and ulna to loosen, due to movement of the radius relative to the ulna, is reduced because of the fusion. It will be obvious to those skilled in the art that many prior devices having various articulating means and means of distal attachment may be adapted for use with the proximal portion of this invention thereby having the advantage of the proximal support of this invention. For example, the articulating means and distal parts of prior devices may be mounted on the distal surface (15c) of the plate shown in FIG. 6a.

FIG. 7 illustrates an intermediate component (18) as shown in FIGS. 3-5. As seen in FIG. 7a, the proximal side of intermediate component (18) is shaped to conform to the curvature of the distal surface of the plate (15c) shown in FIG. 6a with region (29) having a generally planar proximal surface and region (30) having a curved proximal surface. Receptacle portion (31) of intermediate component (18) is enlarged as compared to the remainder of intermediate component (18) as shown in FIG. 7b. The distal side of receptacle portion (31) contains a concave bearing surface (32) as shown in FIGS. 7c and 7d. The perimeter of the concave bearing surface is illustrated in FIG. 7d and is generally oval in shape which provides an ellipsoidal shape to the concave bearing surface (32). As is illustrated in FIG. 7c, the cross-section of the concave bearing surface (32) is generally part-circular.

Intermediate component (18) is preferably made from an orthopedically suitable plastic material such as high density polyethylene. Alternatively, intermediate component (18) may be composed of other orthopedically suitable materials such as metals or ceramic compounds.

The enlargement of the intermediate component (18) in the receptacle portion (31) permits the bearing surface to be of sufficient area for better support of the wrist. Since the remainder of the intermediate component conforms in size and shape to plate (15) the intermediate component will cause minimal interference with the ligamenture of the wrist.

Intermediate component (18) is adapted to be fixed to plate (15) after the plate is attached to the radius and ulna. Various means of attachment of the intermediate component to the plate will be obvious to persons skilled in the art. For example, when the intermediate component (18) is composed of an orthopedically suitable plastic, it may be provided with one or more resilient flanges (40) as is shown in phantom outline in FIG. 7c, which are adapted to engage plate (15). In such an embodiment, intermediate component (18) may be attached to plate (15) merely be pressing it into place. The resilient flange (40) may be a lip or a plurality of tangs. Preferably, plate (15) will have a lip or plurality of tangs, as is illustrated in phantom outline by flange (39) on FIG. 6a, complementary to and adapted to engage with flange (40) on intermediate component (18).

It is preferable that the intermediate component be provided to the surgeon in a variety of sizes which correspond to the variety of sizes of the plate (15). In addition, it will also be preferable if the intermediate component (18) is provided in a variety of sizes having different heights as measured between the proximal and distal surfaces of the component. Thus the intermediate component may be used to size the entire prosthesis within a patient's wrist to provide proper tension on the ligamenture and to provide a center of rotation in an anatomically correct position.

Figure 8A:
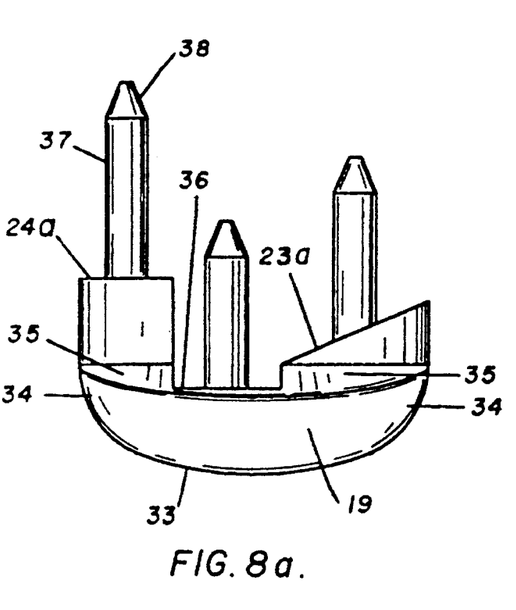
FIG. 8a is a side view showing the longitudinal extent of the distal part.
Figure 8B:
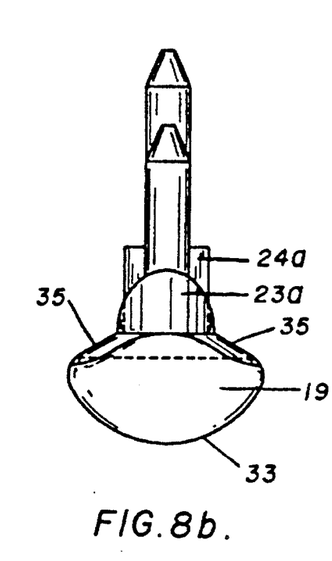
FIG. 8b is a front view; and, FIG. 8c is a top view showing the distal side of the distal part.
Figure 8C:
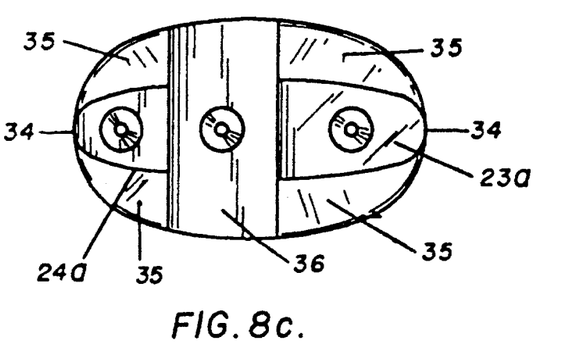

FIG. 8 illustrates the distal part (19) of a most preferred embodiment of the prosthesis of this invention. FIG. 8a shows the distal part in side view. On the proximal side of the distal part (19) there is a convex bearing surface (33) as shown in FIGS. 8a and 8b. It is intended that the convex bearing surface (33) be ellipsoidal in shape with a part-circular cross section complementary to the concave bearing surface (32) of intermediate component (18) shown in FIG. 7. Most preferably, the ellipsoidal shape of convex bearing surface (33) will be modified as shown in FIGS. 8a and 8c. In the latter Figures, the ends (34) of the convex bearing surface (33) are rounded and thus deviate from the elliptical profile complementary with the concave surface of the intermediate component. For example, the rounded ends (34) may be spherical. The rounded ends (34) will permit some rotation of the distal part (19) relative to the intermediate component (18) during radial-ulnar deviation instead of only a lateral translation of the distal part relative to the intermediate component. The latter embodiment will cause less interference with soft tissues surrounding the articulating joint.

As shown in FIGS. 8a–c, relief angles (35) extend distally on both sides of distal part (19) which taper toward the midline of the longitudinal axis of distal part (19). The presence of relief angles (35) permit the bearing surface of the distal part to be large and complementary with the bearing surface of intermediate component (18) while permitting the distal portions of distal part (19) to have a decreased width to prevent interference with surrounding soft tissue.

Referring to FIGS. 8a and 8b, there is illustrated the trapezoid engaging projection (24a) at one end of the distal part (19). This projection has a flat distal face to be supported upon a prepared proximal surface of the trapezoid. At the other end of distal part (19) is the hamate engaging projection (23a) which has a flat distal surface that inclines proximally and medially to be supported on a prepared surface of the hamate. As can be seen in FIG. 8c, the profile of the ends and lateral surfaces of projections (23a) and (24a) are curved. Between projections (23a) and (24a) is the capitate engaging depression (36) which has a generally rectangular shape with a flat bottom. The flat bottom surface of depression (36) extends substantially across the width of relief angle (35).

The preferred shape of distal part (19) described above is such that it complements the proximal surfaces of the distal row of carpal bones after limited shaping of the bone. Other shapes of the distal aspect of the distal part (19) will be apparent which will permit the distal part to be supported on surfaces of the distal carpal bones.

Preferably, the distal part (19) will be supported on at least three of the distal carpal bones for stability. It is preferable that the dimensions of distal part (19) are such that the part will complement with intermediate component (18) to replace the proximal row of carpal bones and will also replace a sufficient portion of the proximal part of the distal carpal bones such that the center of rotation of the prosthesis will be near the head of the capitate. The latter preferred feature requires resection of at least the proximal capitate to bring the center of rotation near the head of the capitate.

Appropriate dimensions of distal part (19) may be determined through anatomical measurements. Three sizes of distal part (19) supplied to the surgeon will be sufficient to permit installation of the prosthesis in most patients. It is also possible to provide a multi-part distal component which, for example, will have separate bearing and distal support parts which will be joined.

As is shown in FIG. 8a, distal part (19) is preferably provided with fixation means for attachment of the part to one or more distal carpal bones. In this embodiment the fixation means are fixed pegs (37) having tapered ends (38) which facilitate centering of the pegs in holes drilled into the distal carpal bones. In order to prevent invasion of the carpal-metacarpal joint, pegs (37) should be of insufficient length to pass through the carpal bones.

Distal component (19) may be composed of any orthopedically suitable material such as metal, plastic or ceramic. The preferred material is an orthopedically suitable metal such as cobalt chromium alloy or titanium. A metallic distal part will provide superior strength and a good bearing surface particularly for articulation in a complementary bearing surface composed of plastic such as high density polyethylene.

It will be appreciated by a person skilled in the art that the distal aspect of this invention as exemplified by distal part (19) may be used in a variety of prosthetic devices having various articulattingmeans and means of proximal attachment. This will provide the advantage of having distal support for the prosthesis spread over at least three carpal bones which will support the prosthesis without the necessity of fixation to one or more metacarpal. If warranted, the fixation means of the distal part of this invention may be extended such that the distal part is supported by the metacarpal bones as well as the carpal bones.

It will also be appreciated by a person skilled in the art that the preferred ellipsoidal articulating surface of this invention wherein the convex bearing surface has rounded ends may be employed in a variety of prosthetic devices having ellipsoidal bearing surfaces and any variety of proximal and distal fixation means. The presence of rounded ends at both ends of the convex bearing surface permits radial-ulnar deviation without excessive lateral translation of the articulating components which results in soft tissue interference.

Procedures for implantation of wrist prostheses are well known. Typically, the wrist is surgically exposed from a dorsal approach. In such a case, a midline dorsal incision is made in the wrist. Superficial soft tissues, including tendons, are retracted radially and ulnarly. The wrist capsule is opened longitudinally and by sharp dissection, the capsule is incised from the distal radius and distal ulna, but left intact, and retracted radially and ulnarly allowing visualization of the carpal bones. Distally, the capsule is also sharply dissected off the distal carpal row of bones and retracted ulnarly and radially. Soft tissue such as triangular fibrocartilage is removed from the distal end of the ulna.

At this stage, the surgical procedures for implantation of a prosthesis of this invention differ from prior methods. To accommodate the preferred distal part (19) of this invention, the scaphoid, lunate, triquetrum are sharply removed in total. To accommodate the use of the proximal part such as plate (15) of this invention, a section of bone is removed from the distal ulna (as shown at gap (20) in FIGS. 3 and 5) to permit pronation and supination once the prosthesis is implanted, unless the patient can tolerate an absence of pronation and supination such as a result of a pre-existing fusion of the radius and ulna. Articular cartilage is removed from the distal radial-ulnar joint (9) as shown in FIG. 1. Bone chips, which may be taken from the ulna resected at gap (20) or from the iliac crest, may be packed into area (17) as shown in FIGS. 3 and 5, to stimulate fusion between the distal radius and distal ulna.

The wrist prosthesis is inserted in stages with the use of jigs and power instruments. Plate (15) is first secured to the prepared distal end of the radius and ulna. In the preferred embodiment described herein, one or more screws are first driven into the radius and a screw is then driven into the elongated through-hole (28) shown in FIG. 6 in order to force the ulna and radius together. In addition, known means for transverse fixation of the radius and ulna (such as wires or screws) may be added. The distal part (19) is then secured to a prepared distal carpal row. The intermediate component (18) is then secured to the base plate (15) with the convex bearing surface of distal part (19) engaged in the concave receptacle of intermediate component (18) as shown in FIGS. 3–5. Now, rotation of the hand, wrist and radius about the ulna (pronation and supination) cannot occur at the distal radial-ulnar joint, but can occur through the gap (20) created in the ulna as shown in FIGS. 3 and 5. This invention permits the ligamenture of the wrist to be mainly preserved which, in conjunction with the enhanced proximal and distal support possible with this invention, will provide enhanced overall support for the wrist while permitting freedom of motion.

Various changes and modifications may be made in practising this invention without departing from the spirit and scope thereof.

We claim:

1. A prosthesis for use in a wrist, the wrist has a distal end of a radius adjacent a distal end of an ulna, said prosthesis comprising a proximal supporting part, a distal part and means for articulating the proximal supporting part with respect to the distal part disposed therebetween, said proximal supporting part including means for supporting and fastening the proximal part on substantially unaltered epiphyses of each of the distal ends of the radius and ulna when said distal ends are fused at a radial-ulnar joint, said means for supporting and fastening having a proximal surface facing away from the distal supporting part of the prosthesis, the proximal surface comprising:

(a) a substantially planar portion extending medially from a first end of the proximal surface, said planar portion configured for being supported on ulnar epiphysis and a portion of radial epiphysis adjacent the ulna epiphysis, and (b) a generally convex curved portion extending medially from a second end of the proximal surface to the planar portion, said second portion configured for being supported on curved epiphyses of the radius.

2. The prosthesis of claim 1, wherein the proximal surface is on a plate with the plate having first means for fastening the plate to epiphyses of the radius at the convex curved portion and second means for fastening the plate to epiphyses of the ulna at the planar portion.

3. The prosthesis of claim 2, wherein the first and second means for fastening comprise holes through the plate configured to receive orthopedic fasteners.

4. The prosthesis of claim 2, wherein the plate comprises an orthopedically suitable metallic material.

5. The prosthesis of claim 2, wherein the proximal part additionally comprises an intermediate component for attachment to a side of the plate facing away from the proximal surface of the plate and wherein the intermediate component supports the means for articulating the proximal supporting part with respect to the distal part.

6. The prosthesis of claim 5, wherein the means for articulating includes first and second bearing surfaces, the first bearing surface having an ellipsoidal convex shape with a generally part-circular cross-section and the second bearing surface having a concave shape complementary to said convex shape, and wherein the second bearing surface is a surface of a receptacle on a side of the intermediate component facing away from the plate.

7. The prosthesis of claim 6, wherein the plate comprises an orthopedically suitable metallic material, and the intermediate component comprises an orthopedically suitable plastic material with a resilient flange configured for engaging with the plate to provide a means of attachment of the intermediate component to the plate.

8. The prosthesis of claim 2, wherein the plate has at least one elongated through-hole with a bevelled perimeter configured to receive a bevel headed fastener, except at one end of said through-hole.

9. The prosthesis of claim 2, wherein the plate has a plurality of notches about its perimeter complementary to regions of bony and soft tissue protuberances on the radial epiphysis.

10. The prosthesis of claim 1, wherein the distal supporting part has a distal side configured for being supported by surfaces on distal carpal bones, a proximal side defining an ellipsoidal convex bearing surface having a generally part-circular cross-section, and means for fastening the distal part to at least one distal carpal bone; the prosthesis further comprising an intermediate component configured for being attached to the proximal supporting part and having a receptacle portion distally defining a concave bearing surface complementary to the ellipsoidal convex bearing surface; and, wherein the distal part and the intermediate component are configured to replace a proximal row of carpal bones and the said convex bearing surface is received in the concave bearing surface when the prosthesis is implanted in a wrist.

11. The prosthesis of claim 10, wherein the ellipsoidal convex bearing surface of the distal part has ends with rounded profiles deviating from an ellipse; and, the concave bearing surface of the intermediate component is complementary to the ellipsoidal portion of the convex bearing surface.

12. A prosthesis for use in a wrist and for replacing proximal carpal bones, said wrist comprising at least a part of each of three distal carpal bones comprising a hamate, a trapezoid and a capitate, the prosthesis comprising a proximal supporting member, a distal supporting member and means for articulating the proximal supporting member with respect to the distal supporting member disposed therebetween, wherein, a first side of said distal supporting member has:

(a) a first projection having a generally planar distal face configured for being supported on the trapezoid, and (b) a second projection having a generally planar distal face that angles proximally and medially and is configured for being supported on the hamate, said first and second projections defining a generally rectangular, flat-bottomed depression configured for engaging with and being supported on the capitate.

13. The prosthesis of claim 12, wherein the means for articulating includes two bearing surfaces, one of said surfaces having an ellipsoidal convex shape with a generally part-circular cross-section and forming a second side of said distal part opposite the first side, the other of said surfaces having a concave shape complementary to said convex shape.

14. The prosthesis of claim 12, wherein the means for articulating includes two bearing surfaces, one of said surfaces forming a second side of said distal part opposite the first side and having an ellipsoidal convex shape with a generally part-circular cross-section with ends of said ellipsoidal shape having a rounded profile deviating from an ellipse and, the other of said bearing surfaces having a concave shape that is complementary to the ellipsoidal convex shape.

15. A part for use as means to support a wrist prosthesis on at least part of each of a hamate, a capitate, and a trapezoid in a wrist, wherein said part has a first side having:

(a) a first projection having a generally planar distal face configured to be supported on the trapezoid, and (b) a second projection having a generally planar distal face that angles proximally and medially and is configured to be supported on the hamate, said first and second projections defining a generally rectangular, flat-bottomed depression configured to engage with and be supported on the capitate;

and, wherein a second side of the part opposite the first side is a convex ellipsoidal bearing surface with a part circular cross section.

16. The part of claim 15 comprising an orthopedically suitable metallic material.

17. The part of claim 16 having a plurality of fastening pins on the first side for fastening the part to one or more of the hamate, capitate and trapezoid.

* * * * *